United States Patent [19]

Schmidt et al.

[11] 3,952,057

[45] Apr. 20, 1976

[54] PROCESS FOR THE PREPARATION OF GUANIDINE CARBONATE

[75] Inventors: Alfred Schmidt; Karlheinz Wegleitner; Josef Herbert Hatzl; Rudolf Sykora; Ferdinand Weinrotter, all of Linz, Danube, Austria

[73] Assignee: Chemie Linz AG, Linz, Austria

[22] Filed: July 3, 1973

[21] Appl. No.: 376,176

[30] Foreign Application Priority Data
July 14, 1972 Germany............................ 2234732

[52] U.S. Cl............................................. 260/564 D
[51] Int. Cl.$^2$........................................ C07C 129/00
[58] Field of Search..................... 260/564 D, 564 A

[56] References Cited
UNITED STATES PATENTS
2,826,613  3/1958  Grosskinsky et al............ 260/564 D FOREIGN PATENTS OR APPLICATIONS
244,345  1965  Austria Primary Examiner—Gerald A. Schwartz
Attorney, Agent, or Firm—Wenderoth, Lind & Ponack

[57] ABSTRACT

Process for obtaining guanidine carbonate from aqueous solutions in which it is present with urea and its pyrolysis products as well as ammonia and carbon dioxide, which comprises heating the aqueous solution to a temperature of at most 80°C at atmospheric pressure, evaporating the resulting solution, which contains an amount of carbon dioxide equal to the guanidine content, until it is saturated with urea, separating the solid precipitate, suspending the mother liquor in liquid ammonia and separating the resulting guanidine carbonate.

5 Claims, No Drawings

PROCESS FOR THE PREPARATION OF GUANIDINE CARBONATE

This invention relates to a process for obtaining guanidine carbonate from aqueous solutions in which it is present together with urea and its pyrolysis products.

In chemical processes involving the pyrolysis of urea, such as, for example, the manufacture of melamine from urea or from cyanic acid, or the manufacture of cyanuric acid from urea, during the course of working up, there may be produced aqueous solutions which contain guanidine in addition to considerable amounts of urea pyrolysis products such as melem, mellone, melam, ammeline, ammelide, cyanuric acid, cyanamide, dicyandiamide, ammonium cyanate, ammonium carbamate and/or ammonium carbonate. In particular, such solutions are obtained if, in the synthesis of melamine from urea or cyanic acid, the reaction gases, containing melamine, which are obtained are quenched with water in a quencher and the sparingly soluble melamine is separated off in the form of a solid, for example as disclosed in Austrian Pat. No. 244,345.

For economic reasons, a re-use of such solutions, for example by concentration and recycling to the urea synthesis, would be desirable but an objection to this is that the guanidine content interferes. On the other hand, the isolation of the guanidine, which is an interesting intermediate product for various chemical synthesis, would be desirable. A usuable process has not hitherto been disclosed and difficulties were also foreseeable since, in the case of working up by customary evaporation, urea decomposes to a considerable extent or condenses with guanidine to give high molecular weight products.

It has now been found that guanidine may be separated from such solutions and isolated in the form of its carbonate, without having to sustain substantial losses of guanidine and/or urea, if, when concentrating the solutions, a temperature of 80°C is not exceeded, the carbon dioxide content of the solution is utilised to form guanidine carbonate, and liquid ammonia is used as the separating agent. The process is also based on the surprising fact that guanidine in aqueous solution, when mixed with urea and the other substances present, is stable to heat, in contrast to its behaviour in pure aqueous solutions. On simple suspension in liquid ammonia, the guanidine carbonate is obtained in such a pure form that in certain cases further purification is superfluous.

Accordingly, the present invention provides a process for obtaining guanidine carbonate from an aqueous solution in which it is present in addition to urea and its pyrolysis products, as well as ammonia and carbon dioxide, especially from mother liquors from the manufacture of melamine from urea or cyanic acid and ammonia, which comprises heating the aqueous solution to a temperature of at most 80°C at atmospheric pressure, to expel the ammonia and free carbon dioxide present, evaporating the resulting solution, which contains an amount of $CO_2$ equivalent to the guanidine content, at a pressure between 0.1 and 0.80 atmospheres absolute and a temperature between 50°C and 80°C until the solution, after cooling to a temperature of 20°C to 30°C, is saturated with urea, separating the resulting solid precipitate and then suspending the remaining solution, if desired, after further evaporation at a pressure between 0.1 and 0.80 atmospheres absolute and a temperature of 50°C to 80°C, which must be carried out to a water content between 10% and dryness within 5 seconds, in an amount of liquid ammonia which is at least twice the amount of urea present, the water content of the suspension not being allowed to exceed 20% by weight, and then separating in a conventional manner the guanidine carbonate which remains undissolved.

The expelling of ammonia and carbon dioxide is performed usually at temperatures as high as possible without exceeding the maximum temperature of 80°C. If this step is carried out at lower temperatures, for example about 60°C, it will be more time consuming.

The concentration of urea in the aqueous solution at which saturation is reached at a temperature of about 30°C, is 40 to 50% by weight, since the guanidine present somewhat lowers the solubility of urea.

If melamine is present in the mixture, the bulk thereof precipitates at this point, that is to say on cooling the concentrate to a temperature of 20° to 30°C, and may be separated off. It is sufficiently pure so that after the customary recrystallisation from water it may be used for any desired purpose.

During the further evaporation operation it is to be borne in mind that the objectionable condensation of urea with guanidine may be avoided, unless special measures are taken, only if during evaporation a temperature of 80°C and a water content of 10% by weight, relative to the concentrate, are not exceeded. However in many cases it suffices in any case to lower the water content to a value between 10 and 20% by weight relative to the ammonia suspension and to carry out the separation by means of liquid ammonia, according to the invention, with this concentrate. If, however, it is desired to carry out the separation on products of water content lower than 10% by weight relative to the concentrate or on a completely dry product, it is necessary to lower the amount of water to below 10% by weight by evaporation within 5 seconds, which may be achieved, for example, by means of spray drying.

The amount of liquid ammonia which is required to suspend the dry solids or the solids concentrate which still contains water, which are obtained, depends firstly on its urea content and on the water content of the product, and also on the temperatures and pressures at which the suspension of the mixture of substances and the isolation of the guanidine carbonate are carried out. In general, the amount will be up to four times the amount of urea present. The separation of the guanidine carbonate from the urea and the remaining admixture in liquid ammonia is appropriately carried out at a temperature between −33°C and +20°C, and a pressure between atmospheric pressure and about 10 atmospheres absolute may be used.

The process according to the invention is illustrated in the following Examples.

EXAMPLE 1

In the catalytic production of melamine from cyanic acid 3 tons of a mother liquor are obtained hourly after removing the bulk of the melamine; the mother liquor has approximately the following composition by weight:

11.0% of $NH_3$
8.5% of $CO_2$
6.0% of urea
1.45% of guanidine 0.65% of residual melamine and various pyrolysis products
Remainder: water In order to be able to evaporate the solution in vacuo, it is necessary first to remove the excess ammonia and carbon dioxide at atmospheric pressure. Two tons of a solution which has approximately the following weight composition are obtained hourly:
0.3% of $NH_3$
1.2% of $CO_2$
8.2% of urea
2.2% of guanidine
1.52% of residual melamine and various pyrolysis products
Remainder: water.

In this evaporation process, only about 10% of the urea is lost.

This concentrated mother liquor is further concentrated in a vacuum concentrator at a pressure of 0.26 atmosphere absolute and a sump temperature of 67°C, to avoid further losses of urea, 0.4 ton of a concentrate being obtained hourly; this concentrate has approximately the following composition by weight:
0.05% of $NH_3$
41.0% of urea
16.2% of guanidine carbonate
7.6% of melamine and various pyrolysis products
Remainder: water This concentrate is cooled to 25°C, whereupon about 7.5 kg of melamine crystallise out in 95% purity. After separating off the melamine, the concentrated mother liquor which remains is cooled further, whereupon further solids precipitate, and is suspended, at about −33°C, in 700 kg of liquid ammonia under atmospheric pressure. The solid which precipitates is filtered off, washed with 50 kg of liquid ammonia and dried. About 65 kg of guanidine carbonate, which is more than 99% pure, are obtained hourly.

EXAMPLE 2

In a procedure analogous to that described in Example 1, a melamine mother liquor having the same composition as described in Example 1 is first freed of excess ammonia and carbon dioxide under normal pressure and is evaporated at 0.26 atmosphere absolute and a sump temperature of 67°C, the concentrate is cooled, the bulk of the melamine remaining in the mother liquor is separated off and the liquor is further evaporated in vacuo. About 290 kg of a mixture of the weight composition shown below are obtained hourly:
57% of urea
22% of guanidine carbonate
7% of melamine and other pyrolysis products
Remainder: water This mixture is evaporated over the course of 4 seconds in a spray drier at 0.1 atmosphere absolute and 50°C. 250 kg of a product having approximately the following composition by weight are obtained hourly:
66% of urea
25% of guanidine carbonate
8% of residual melamine and various pyrolysis products
< 1% of residual moisture.

The small amount of residual moisture which remains does not lead to any significant and undesired reaction between the urea and guanidine carbonate.

The solid is suspended in about 660 kg of liquid ammonia at about −33°C and atmospheric pressure, stirred for 10 minutes, filtered off and washed with 50 kg of liquid ammonia. After drying at 90°C, about 65 kg of 99% pure guanidine carbonate are obtained hourly.

What we claim is:

1. A process for obtaining guanidine carbonate from an aqueous solution containing guanidine, urea, pyrolysis products of urea, ammonia and carbon dioxide, which comprises heating the aqueous solution to a temperature not higher than 80°C at atmospheric pressure to expel the ammonia and free carbon dioxide present in the aqueous solution, evaporating the resulting solution containing an amount of carbon dioxide equivalent to the guanidine content thereof at a pressure between 0.1 and 0.80 atmospheres absolute and a temperature between 50°C and 80°C until the solution, after cooling to a temperature of 20° to 30°C, is saturated with urea, separating the resulting solid precipitate from the solution, suspending the remaining solution, at a temperature between −33°C and 20°C, in an amount of liquid ammonia which is at least twice the amount of urea present in the solution, the water content of the resultant suspension being not higher than 20% by weight, and separating undissolved guanidine carbonate from the suspension.

2. A process according to claim 1, in which the amount of liquid ammonia is 2 to 4 times by weight based on the amount of urea.

3. A process according to claim 1, in which the suspension in liquid ammonia is conducted at a pressure of 1 to 10 atmospheres absolute.

4. A process according to claim 1, in which the solution remaining after separating the resulting solid precipitate is, prior to the suspension in liquid ammonia, further evaporated within 5 seconds to a water content of less than 10% at a pressure between 0.1 and 0.80 atmospheres absolute and a temperature between 50°C and 80°C.

5. A process according to claim 1, in which the initial aqueous solution is the aqueous mother liquors resulting from a process for producing melamine by reaction of urea or cyanic acid and ammonia, which aqueous solution consists essentially of guanidine, urea, pyrolysis products of urea, ammonia and carbon dioxide.

* * * * *